United States Patent
Choi (10) Patent No.: US 10,646,273 B2
(45) Date of Patent: May 12, 2020

(54) APPARATUS FOR IRRADIATING LASER

(71) Applicant: LAMEDITECH CO., LTD., Seoul (KR)

(72) Inventor: Jong Seok Choi, Incheon (KR)

(73) Assignee: Lameditech Co., Ltd., Seoul (KR)

( * ) Notice: Subject to any disclaimer, the term of this patent is extended or adjusted under 35 U.S.C. 154(b) by 0 days.

(21) Appl. No.: 15/117,057

(22) PCT Filed: Mar. 28, 2016

(86) PCT No.: PCT/KR2016/003099
§ 371 (c)(1),
(2) Date: Aug. 5, 2016

(87) PCT Pub. No.: WO2016/159599
PCT Pub. Date: Oct. 6, 2016

(65) Prior Publication Data
US 2017/0172659 A1    Jun. 22, 2017

(30) Foreign Application Priority Data
Apr. 2, 2015 (KR) .......................... 10-2015-0046806

(51) Int. Cl.
*A61B 18/20* (2006.01)
*A61B 5/151* (2006.01)
(Continued)

(52) U.S. Cl.
CPC ...... *A61B 18/203* (2013.01); *A61B 5/150022* (2013.01); *A61B 5/15138* (2013.01);
(Continued)

(58) Field of Classification Search
CPC ................ A61B 18/20; A61B 18/203; A61B 2017/00017; A61B 2018/00196;
(Continued)

(56) References Cited

U.S. PATENT DOCUMENTS 3,383,491 A    5/1968  Muncheryan
3,622,743 A *  11/1971 Muncheryan ...... B23K 26/0096
                                                   606/2

(Continued)

FOREIGN PATENT DOCUMENTS

JP    63268588 A    11/1988
JP    01124454 A    5/1989
(Continued)

OTHER PUBLICATIONS

European Search Report for EP application No. 16773380.7, dated Dec. 14, 2018.

*Primary Examiner* — Carl H Layno
*Assistant Examiner* — Erin M Piateski
(74) *Attorney, Agent, or Firm* — Greer Burns & Crain Ltd.

(57) ABSTRACT

The apparatus for irradiating a laser in accordance with an exemplary embodiment includes: a main body; a laser resonator located within the main body and configured to generate a laser beam and output the laser beam forwards; a beam barrel in which a focusing lens is fixed; a beam barrel guiding unit located in front of the main body and configured to guide forward and backward movement of the beam barrel; and a forward and backward moving means connected to an outer periphery of the beam barrel and configured to move the beam barrel forwards and backwards relative to an irradiation target portion in front of the beam barrel. A screw thread is formed on the outer periphery of the beam barrel and a screw thread is formed on an inner surface of the forward and backward moving means.

9 Claims, 9 Drawing Sheets

(51) Int. Cl.
*A61B 5/15* (2006.01)
*A61B 17/00* (2006.01)
*A61B 18/00* (2006.01)

(52) U.S. Cl.
CPC ........ *A61B 5/150175* (2013.01); *A61B 18/20* (2013.01); *A61B 2017/00017* (2013.01); *A61B 2018/0047* (2013.01); *A61B 2018/00196* (2013.01); *A61B 2018/00202* (2013.01); *A61B 2018/00452* (2013.01); *A61B 2018/00791* (2013.01); *A61B 2018/206* (2013.01)

(58) Field of Classification Search
CPC ........... A61B 2018/00791; A61B 2018/00202; A61B 2018/00452; A61B 2018/0047; A61B 2018/206
USPC ...................................................... 606/2–19
See application file for complete search history.

(56) References Cited

U.S. PATENT DOCUMENTS

| | | | |
|---|---|---|---|
| 4,808,789 A | 2/1989 | Muncheryan | |
| 4,913,132 A * | 4/1990 | Gabriel | A61B 1/227 606/17 |
| 6,490,083 B1 * | 12/2002 | McManus | A61B 1/3135 359/376 |
| 6,790,205 B1 | 9/2004 | Yamazaki et al. | |
| 7,309,335 B2 * | 12/2007 | Altshuler | A61B 18/203 606/9 |
| 7,384,405 B2 * | 6/2008 | Rhoades | A45D 24/007 601/137 |
| 2006/0268423 A1 | 11/2006 | Ho | |
| 2007/0260230 A1 * | 11/2007 | Youngquist | A61B 18/203 606/9 |
| 2012/0226268 A1 * | 9/2012 | Liu | A61B 18/203 606/9 |

FOREIGN PATENT DOCUMENTS

| | | |
|---|---|---|
| JP | 01245988 A | 10/1989 |
| JP | 2000-60869 A | 2/2000 |
| JP | 2005224502 A | 8/2005 |
| KR | 10-2007-0044621 A | 4/2008 |
| KR | 10-1224220 B1 | 1/2013 |
| KR | 10-1437540 B1 | 8/2014 |

* cited by examiner

APPARATUS FOR IRRADIATING LASER

PRIORITY

This application is a U.S. National Phase Application pursuant to 35 U.S.C. § 371 of International Application No. PCT/KR2016/003099 filed Mar. 28, 2016, and also claims priority to Korean Patent Application No. KR-10-2015-0046806, filed on Apr. 2, 2015. The entire disclosure contents of these applications are herewith incorporated by reference into the present application.

TECHNICAL FIELD

The present disclosure relates to an apparatus for irradiating a laser.

BACKGROUND

Recently, as various medical devices have been developed along with the development of various high technologies, high-tech laser devices are being used more often than ever before in the medical field to treat various diseases.

One of the uses of a medical laser is to perforate skin by irradiating a laser to the skin in order to collect blood from the perforated skin, administer a drug into a perforation, or remove dots or freckles from the skin.

Further, in the field of dentistry, particularly, for the treatment of caries, a laser device enables a non-contact treatment with a higher accuracy unlike a drill necessarily requiring a mechanical contact. Furthermore, the laser device can minimize pain mainly caused by vibration or heat in a mechanical contact and thus more easily achieve a painless treatment. Therefore, in recent years, laser devices have completely or partially substituted for conventional mechanical devices such as drills.

In this regard, Korean Patent Laid-open Publication No. 2007-0044621 (entitled "Medical laser irradiator and irradiation method") discloses a configuration including an adapter for supplying electrical power, a main body configured to generate a laser with an output intensity selected by a user, and a handpiece configured to irradiate the laser generated by the main body.

DISCLOSURE OF THE INVENTION

Problems to be Solved by the Invention

The present disclosure is conceived to solve the above-described problem of the conventional technology, and provides an apparatus for irradiating a laser with which it is possible to select a depth and a size of a laser perforation and also possible to suppress infection by replacing and using an anti-contamination cap.

However, problems to be solved by the present disclosure are not limited to the above-described problems. There may be other problems to be solved by the present disclosure.

Means for Solving the Problems

According to an aspect of the present disclosure, an apparatus for irradiating a laser includes: a main body; a laser resonator located within the main body and configured to generate a laser beam and output the laser beam forwards; a beam barrel in which a focusing lens is fixed; a beam barrel guiding unit located in front of the main body and configured to guide forward and backward movement of the beam barrel; and a forward and backward moving means connected to an outer periphery of the beam barrel and configured to move the beam barrel forwards and backwards relative to an irradiation target portion in front of the beam barrel. A screw thread is formed on the outer periphery of the beam barrel and a screw thread is formed corresponding to the screw thread of the beam barrel on an inner surface of the forward and backward moving means to rotate the forward and backward moving means, so that the beam barrel is slidably moved forwards and backwards.

Effects of the Invention

According to the aspect of the present disclosure, it is possible to precisely select a size and a depth of a perforation formed by a laser beam irradiated to an irradiation target portion by moving the beam barrel forwards and backwards.

Further, it is possible to suppress infection between patients by replacing and using an anti-contamination cap for each patient.

MODE FOR CARRYING OUT THE INVENTION

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the another element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Hereinafter, the present disclosure will be described in detail with reference to the accompanying drawings.

Figure 1:
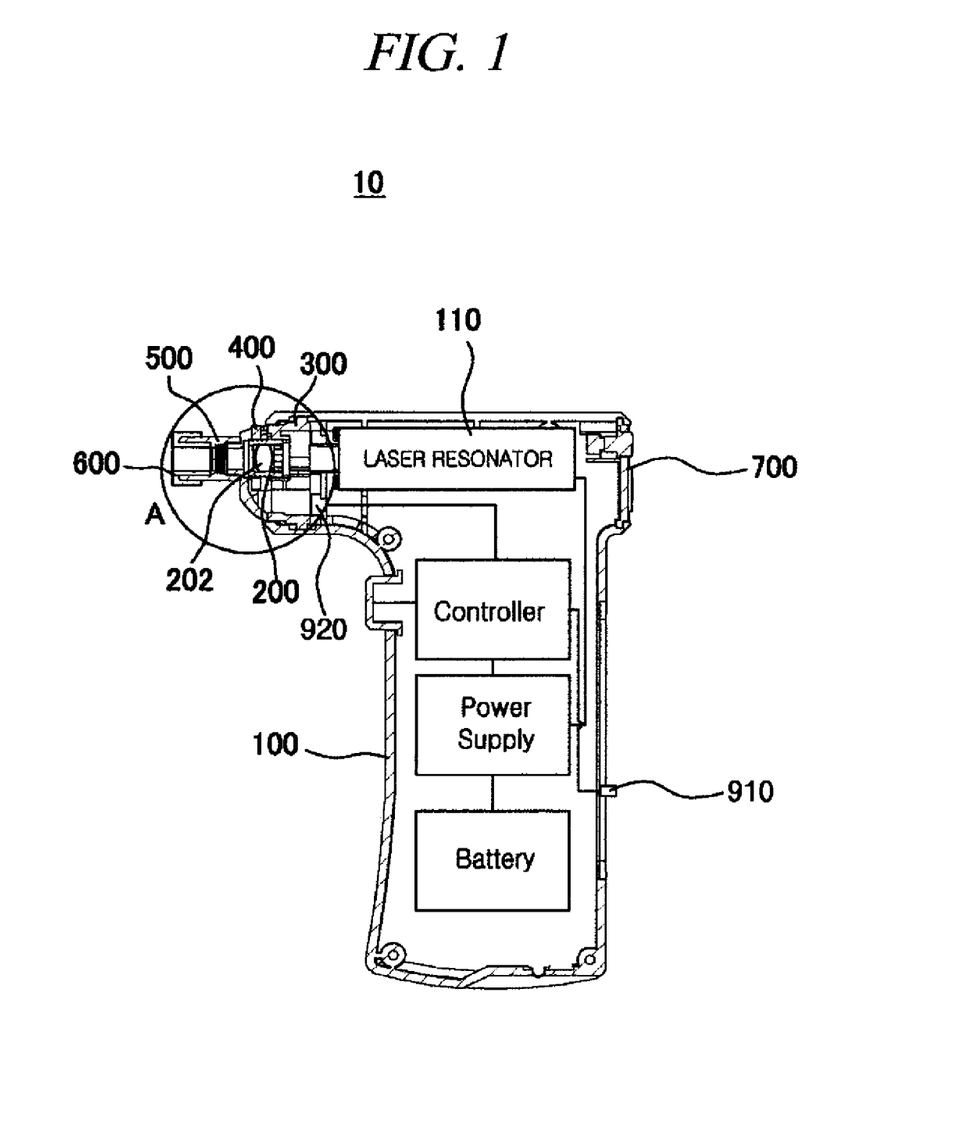
FIG. 1 is a cross-sectional view of an apparatus for irradiating a laser in accordance with an exemplary embodiment.
Figure 2:
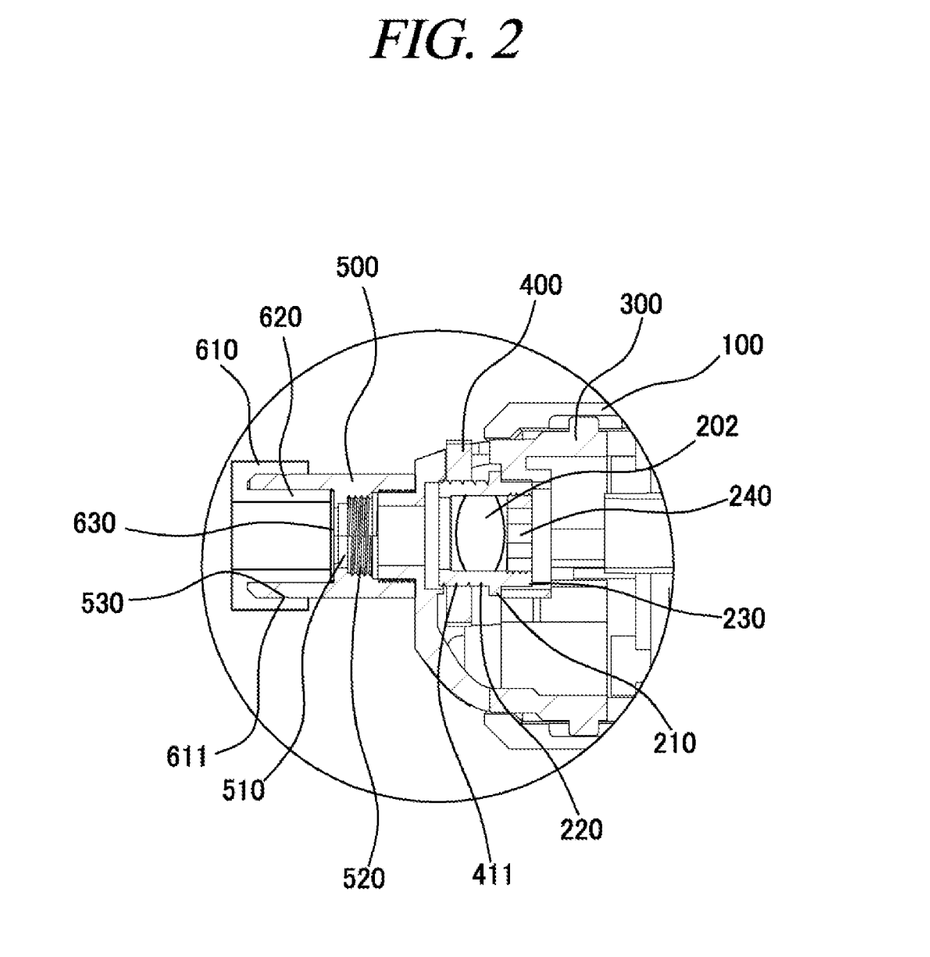
FIG. 2 is an enlarged view of an area A of FIG. 1.
Figure 3:
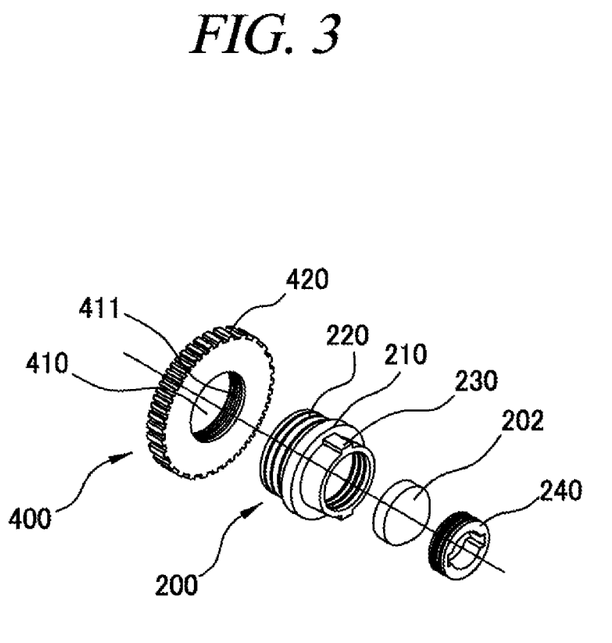
FIG. 3 is an exploded view of a beam barrel and a forward and backward moving means in accordance with an exemplary embodiment.
Figure 4:
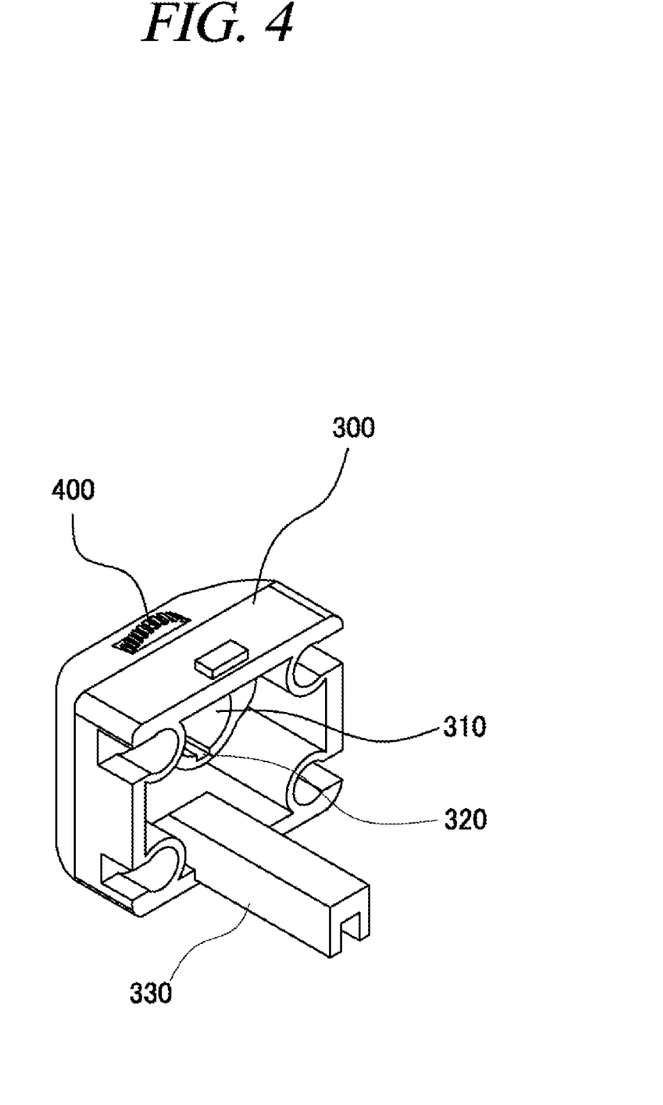
FIG. 4 is a perspective view of a beam barrel guiding unit in accordance with an exemplary embodiment.
Figure 5:
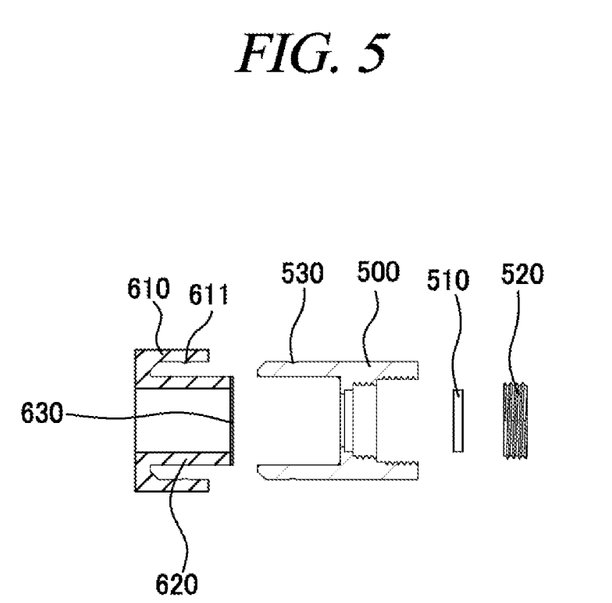
FIG. 5 is an exploded view of an anti-contamination cap and a window part in accordance with an exemplary embodiment.
Figure 6:
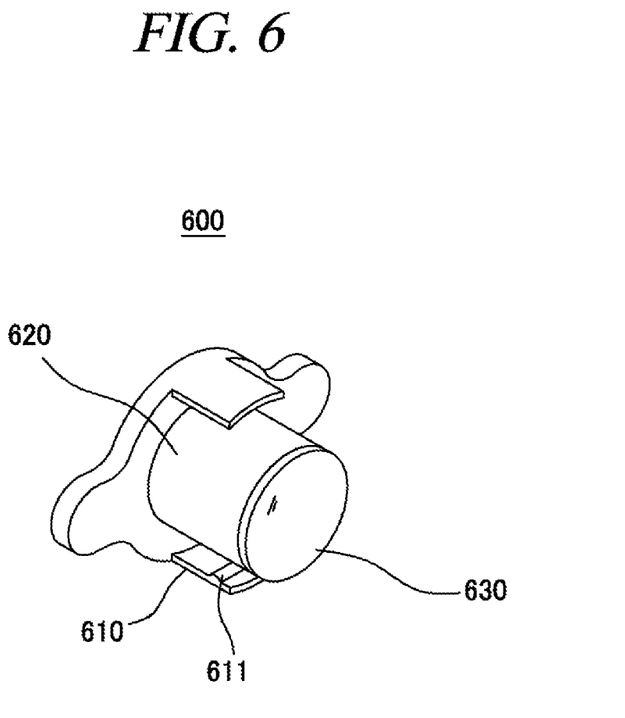
FIG. 6 is a perspective view of the anti-contamination cap in accordance with an exemplary embodiment.
Figure 7:
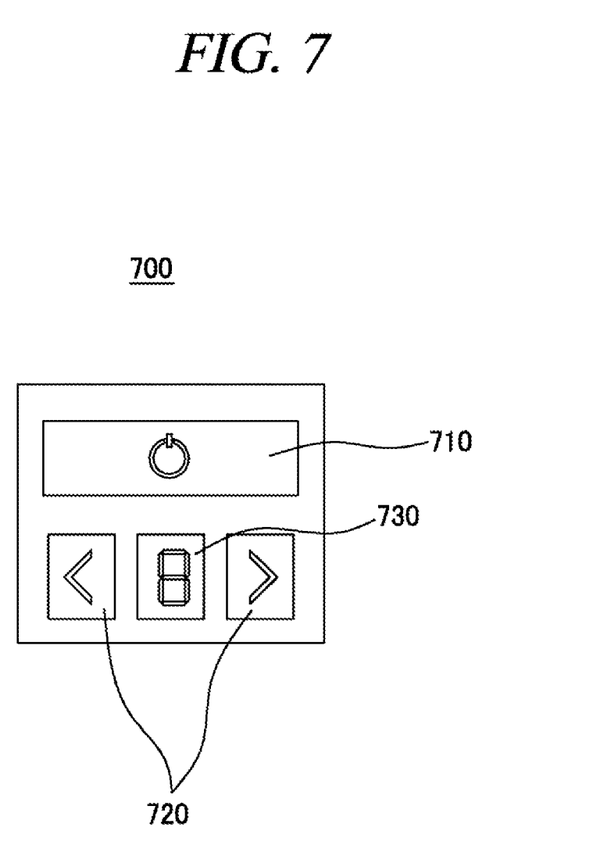
FIG. 7 is a front view of a controller in accordance with an exemplary embodiment.
Figure 8:
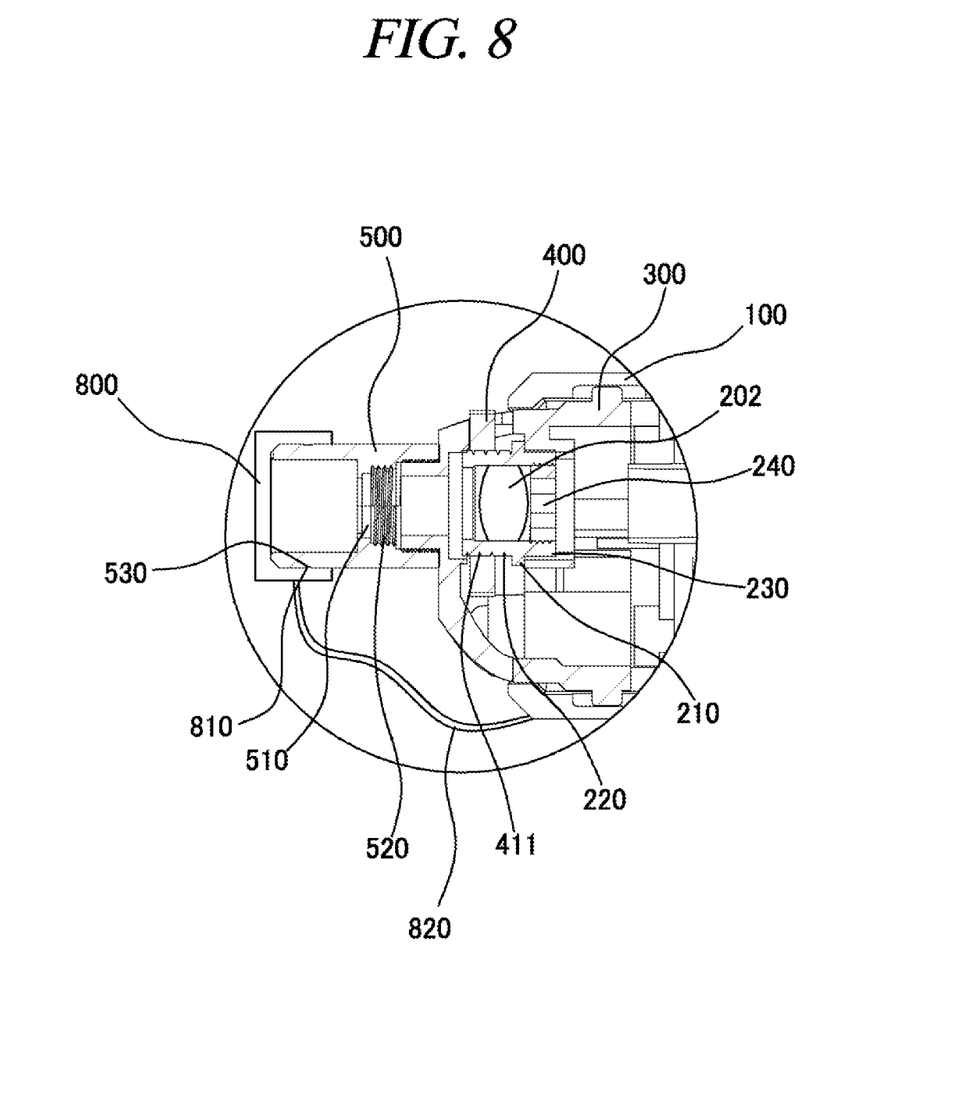
FIG. 8 is a partially exploded view of an apparatus for irradiating a laser to which a cover part is added in accordance with an exemplary embodiment.
Figure 9:
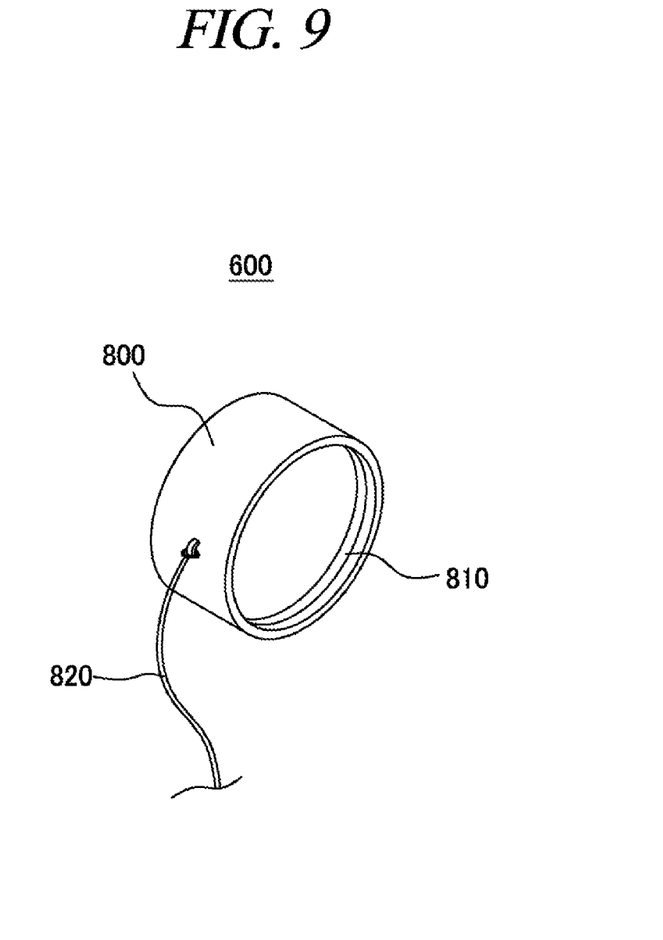
FIG. 9 is a perspective view of the cover part in accordance with an exemplary embodiment.

FIG. 1 is a cross-sectional view of an apparatus for irradiating a laser in accordance with an exemplary embodiment, FIG. 2 is an enlarged view of an area A of FIG. 1, FIG. 3 is an exploded view of a beam barrel and a forward and backward moving means in accordance with an exemplary embodiment, FIG. 4 is a perspective view of a beam barrel guiding unit in accordance with an exemplary embodiment, FIG. 5 is an exploded view of an anti-contamination cap and a window part in accordance with an exemplary embodiment, FIG. 6 is a perspective view of the anti-contamination cap in accordance with an exemplary embodiment, FIG. 7 is a front view of a controller in accordance with an exemplary embodiment, FIG. 8 is a partially exploded view of an apparatus for irradiating a laser to which a cover part is added in accordance with an exemplary embodiment, and FIG. 9 is a perspective view of the cover part in accordance with an exemplary embodiment.

Referring to FIG. 1 and FIG. 2, an apparatus 10 for irradiating a laser in accordance with an exemplary embodiment (hereinafter, referred to as "present laser irradiation apparatus 10") will be described.

Referring to FIG. 1, the present laser irradiation apparatus 10 may include a main body 100, a laser resonator 110, a beam barrel 200, a beam barrel guiding unit 300, and a forward and backward moving means 400.

The laser resonator 110 is located within the main body 100 and configured to generate light energy and output the light energy forwards.

For example, the laser resonator 110 may receive electrical energy and amplify light to generate light energy such as a laser selected from a gas laser, a liquid laser, a solid laser, and a semiconductor laser and then output the laser to the outside.

The laser resonator 110 as described above has a configuration generally used and obvious to those skilled in the art. Therefore, a detailed explanation thereof will be omitted.

The beam barrel 200 is located in front of the laser resonator 110, and a focusing lens 202 is arranged within the beam barrel 200.

The focusing lens 202 is arranged in front of the laser resonator 110 and configured to collect a laser beam incident from the laser resonator 110 and irradiate the laser beam forwards.

Further, the focusing lens 202 may be fixed within the beam barrel 200 by a lens fixing part 240.

The beam barrel 200 provides a path through which a laser beam irradiated from the laser resonator 110 passes and is irradiated to the irradiation target portion.

The beam barrel guiding unit 300 is located in front of the main body and configured to guide forward and backward movement of the beam barrel 200.

In other words, the beam barrel guiding unit 300 includes therein a predetermined space in which the beam barrel 200 is located, and the beam barrel 200 is inserted into a sliding hole 310 and guided to move forwards and backwards.

The forward and backward moving means 400 moves the beam barrel 200 forwards and backwards to select a distance between the irradiation target portion and the focusing lens 202. Thus, a spot size of a laser beam irradiated to the irradiation target portion can be selected.

To be more specific, a screw unit 220 is formed on an outer periphery of the beam barrel 200 and a screw thread 411 is formed corresponding to the screw unit 220 of the beam barrel 200 on an inner periphery of the forward and backward moving means 400 to rotate the forward and backward moving means 400, so that the beam barrel 200 is slidably moved forwards and backwards.

Herein, the term "front" may refer to a direction in which a laser beam is irradiated (9 o'clock direction in FIG. 1) and the term "back" may refer to a direction opposite to the front (3 o'clock direction in FIG. 1).

Referring to FIG. 2 to FIG. 4, a movement of the beam barrel 200 in accordance with an exemplary embodiment will be described in detail.

Referring to FIG. 3, the beam barrel 200 may include a sliding fixing part 210 protruded from a central portion of the outer periphery, the screw unit 220 formed along an outer peripheral surface on one side of the sliding fixing part 210, and a sliding protruding part 230 protruded forwards and backwards on the other side of the sliding fixing part 210.

Herein, the term "one side" may refer to the front (10 o'clock direction in FIG. 3) and the term "other side" may refer to the back (4 o'clock direction in FIG. 3), but may not be limited thereto. The one side may be the back and the other side may be the front. In other words, the screw unit 220 of the beam barrel 200 may be formed at the back of an outer peripheral surface of the beam barrel 200 and the sliding protruding part 230 of the beam barrel 200 may be formed at the front of the outer peripheral surface of the beam barrel 200.

The forward and backward moving means 400 may include a barrel insertion hole 410 into which the screw unit 220 of the beam barrel 200 is inserted, and a screw thread 411 may be formed to be screw-connected to the screw unit 220 of the beam barrel 200 on an inner periphery of the barrel insertion hole 410.

The forward and backward moving means 400 is screw-connected to an outer peripheral surface on one side of the beam barrel 200, and the beam barrel 200 is moved forwards and backwards by rotation of the forward and backward moving means 400. Thus, it is possible to precisely select a location of the focusing lens 202.

Further, the beam barrel 200 may include a lens fixing part 240 which is screw-connected to the beam barrel 200 in order to fix the focusing lens 202. Herein, desirably, the lens fixing part 240 may include a perforation (not assigned a reference numeral) at a central portion in order not to be influenced by a laser beam irradiated from the laser resonator 110 to the focusing lens 202.

The forward and backward moving means 400 may be fixed within the beam barrel guiding unit 300 so as to be rotatable without forward and backward movement, and the screw thread 411 formed on the inner periphery of the forward and backward moving means 400 and the screw unit 220 of the beam barrel 200 may be screw-connected to each other.

That is, when the forward and backward moving means 400 is rotated clockwise or counterclockwise, the beam barrel 200 may be moved toward the front or the back.

Further, the forward and backward moving means 400 includes a concavo-convex part 420 on an outer peripheral surface. Thus, a user can readily rotate the forward and backward moving means 400.

For example, a downward groove is formed at an upper part of the beam barrel guiding unit 300, and the concavo-convex part 420 of the forward and backward moving means 400 is exposed through the groove. Thus, the user can rotate the concavo-convex part 420. However, the present disclosure is not limited thereto. The groove may be formed at a lateral surface or a lower part the beam barrel guiding unit 300, and the concavo-convex part 420 of the forward and backward moving means 400 may be exposed through the groove formed at the lateral surface or the lower part.

Referring to FIG. 4, the beam barrel guiding unit 300 may include a sliding hole 310 into which the other side of the beam barrel 200 is inserted.

Further, a sliding groove 320 into which the sliding protruding part 230 of the beam barrel 200 is inserted may be formed in the sliding hole 310.

In other words, the other side of the beam barrel 200 may be inserted into the sliding hole 310 and the beam barrel 200 may be guided to slidably move forwards and backwards. Further, when the sliding protruding part 230 is inserted into the sliding groove 320, a rotation movement of the beam barrel 200 may be stopped. Thus, if the forward and backward moving means 400 is rotated, the beam barrel 200 is not rotated but slid forwards and backwards.

Further, the sliding fixing part 210 of the beam barrel 200 is formed to have a greater diameter than the sliding hole 310. Thus, the sliding fixing part 210 may be brought into contact with a front portion of the sliding hole 310 to restrict a scope of movement to the back of the beam barrel 200.

An elastic body may be interposed between the front of the main body 100 and the back of the beam barrel guiding unit 300 in order to readily push the beam barrel guiding unit 300 backwards in a predetermined scope.

The beam barrel guiding unit 300 may further include a pressurizing protruding part 330 protruded from the back of the beam barrel guiding unit 300.

A push sensor (920) is located at the back of the beam barrel guiding unit 300. If the beam barrel guiding unit 300 is pushed backwards, the pressurizing protruding part 330 may pressurize the push sensor 920. In this case, the present laser irradiation apparatus 10 irradiates a laser beam when the push sensor 920 detects a contact with the irradiation target portion, and, thus, the present laser irradiation apparatus 10 can suppress safety accidents.

Hereinafter, a window barrel 500 and an anti-contamination cap 600 in accordance with an exemplary embodiment will be described with reference to FIG. 5 and FIG. 6.

The window barrel 500 may be connected to the front of the beam barrel guiding unit 300 and may allow a laser beam passing through the beam barrel 200 to pass therethrough.

For example, the window barrel 500 may include a perforation in a forward and backward direction and also include a screw thread formed at the back of an inner periphery, and thus can be screw-connected to the front of the beam barrel guiding unit 300.

Further, the window barrel 500 may include a window part 510 which is located within the window barrel 500 and a window fixing part 520 which is screw-connected to the window barrel 500 in order to fix the window part 510.

The window part 510 may be manufactured using a transparent material in order to irradiate a laser beam passing through the beam barrel 200 toward the front of the window barrel 500. Further, the window fixing part 520 may include a perforation in order not to be influenced by a laser beam.

The window part 510 can suppress penetration of foreign substance, such as dust, into the beam barrel guiding unit 300 where the focusing lens 202 is located when the laser irradiation apparatus 10 is in storage without being used.

The anti-contamination cap 600 may be connected to the front of the window barrel 500 and configured to suppress contamination of the window 510.

To be more specific, the anti-contamination cap 600 may include an external insertion part 610 to be inserted into an outer periphery of the window barrel 500, an internal insertion part 620 to be inserted into window barrel 500, and a barrier film 630 combined with an end of the internal insertion part 620.

Further, a protrusion part 611 to be engaged with a concave groove 530 formed on an outer surface of the window barrel 500 is formed on an inner surface of the external insertion part 610. Thus, it is possible to suppress unintended separation of the anti-contamination cap 600 during an operation.

If the anti-contamination cap 600 is combined with the window barrel 500, a predetermined space is formed between the barrier film 630 and the window part 510. Thus, it is possible to suppress safety accidents caused by a gas generated from the barrier film 630 by a laser beam.

The anti-contamination cap 600 is replaceably connected to the front of the window barrel 500. Thus, it is possible to suppress infection between patients by replacing and using the anti-contamination cap 600 for each patient.

Hereinafter, a controller 700 in accordance with an exemplary embodiment will be described with reference to FIG. 1 and FIG. 7.

The apparatus 10 for irradiating a laser may include the controller 700 configured to control an operation of the apparatus 10 for irradiating a laser.

The controller 700 may include a power switch 710, an intensity selector 720, and a display part 730.

The power switch 710 may turn on and off a power supply serving as a laser beam energy source.

The intensity selector 720 may select an intensity of a laser beam generated by the laser resonator 110.

The display part 730 may display the intensity selected by the intensity selector 720. For example, the display part 730 may display an intensity of a laser beam in numbers.

The power switch 710 and the intensity selector 720 may be physical buttons or touch panels, and the display part 730 may be a liquid crystal display. However, the present disclosure is not limited thereto. The power switch 710, the intensity selector 720, and the display part 730 may be displayed on one touch display. When the user touches the touch display, power supply or an intensity of a laser beam can be selected.

The controller 700 is located on a back surface of the main body 100 facing a direction in which a laser beam is output, and controls an operation of the present laser irradiation apparatus 10.

In other words, the controller 700 is located on the back surface of the main body 100, so that the user can manipulate the controller 700 while gripping the present laser irradiation apparatus 10.

Referring to FIG. 8 and FIG. 9, the present laser irradiation apparatus 10 may further include a cover part 800 connected to the front of the window barrel 500.

The cover part 800 includes a cover fixing part 810 formed on an inner periphery and engaged with the concave groove 530 formed on the outer surface of the window barrel 500. Thus, it is possible to suppress unintended separation of the cover part 800.

Further, the cover part 800 may include a loss prevention wire 820 of which one side is connected to the cover part 800 and the other side is connected to the main body 100. Thus, it is possible to suppress loss of the cover part 800.

The present laser irradiation apparatus 10 may further include one or more of a grip sensor 910 configured to detect a grip of an operator, a contact sensor configured to detect a contact with the irradiation target portion, and a push sensor 920 configured to detect a backward push of the beam barrel guiding unit 300.

The grip sensor 910 may be one of a photo sensor in which a light is blocked by a gripping hand of a user, a heat sensor configured to detect heat of the gripping hand, and a pressure sensor configured to detect a pressure of the gripping hand.

The contact sensor may be one of a current sensor configured to detect a micro-current flowing in the human body in case of a contact with skin and a temperature sensor configured to detect a temperature of skin in contact with the sensor.

The push sensor 920 may be a pressurization sensor configured to detect pressurization of the beam barrel guiding unit 300 to be pushed backwards.

Further, if a signal detected by at least one of the grip sensor 910, the contact sensor, and the push sensor 920 is shorted, the present laser irradiation apparatus 10 may stop the operation of the laser resonator 110.

The present laser irradiation apparatus 10 may include a battery configured to supply electrical power, a power supply configured to convert the electric power discharged from the battery into electrical power for generation of a laser beam and supply the converted electrical power to the laser resonator 110, and a controller configured to control the laser irradiation apparatus.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

I claim:

1. An apparatus for irradiating a laser, comprising:
a main body;
a laser resonator located within the main body and configured to generate a laser beam and output the laser beam forwards;
a beam barrel which is arranged in front of the laser resonator and in which a focusing lens is fixed;
a beam barrel guiding unit located in front of the main body and configured to guide forward and backward movement of the beam barrel;
a forward and backward moving means connected to an outer periphery of the beam barrel and configured to move the beam barrel forwards and backwards relative to an irradiation target portion in front of the beam barrel;
a window barrel which is connected to the front of the beam barrel guiding unit and allows a laser beam passing through the beam barrel to pass therethrough,
wherein the beam barrel includes:
a sliding fixing part protruded from a central portion of the outer peripheral surface;
a screw unit formed along the outer peripheral surface in front of the sliding fixing part; and
a sliding protruding part protruded from the outer peripheral surface in the back of the sliding fixing part, extended forwards and backwards; and
an anti-contamination cap which is connected to the front of the window barrel and configured to suppress contamination of the window,
wherein the beam barrel guiding unit includes a sliding hole into which the beam barrel is inserted, and a sliding groove into which the sliding protruding part is inserted formed in the sliding hole, so that the beam barrel is guided to slidably move forwards and backwards and a rotation movement of the beam barrel is prevented,
wherein the sliding fixing part is formed to have a greater diameter than the sliding hole to restrict a scope of movement to the back of the beam barrel,
wherein a screw thread is formed corresponding to the screw unit of the beam barrel on an inner surface of the forward and backward moving means to rotate the forward and backward moving means, so that the beam barrel is slidably moved forwards and backwards with respect to the window barrel and the anti-contamination cap exposed to patients.

2. The apparatus for irradiating a laser of claim 1, wherein the forward and backward moving means includes:
a barrel insertion hole including a screw thread on an inner periphery in order to be connected to the screw unit of the beam barrel; and
a concavo-convex part formed along an outer periphery.

3. The apparatus for irradiating a laser of claim 1, wherein the beam barrel includes a lens fixing part which is screw-connected to the beam barrel in order to fix the focusing lens.

4. The apparatus for irradiating a laser of claim 1, wherein the window barrel includes:
a window part which is located within the window barrel; and
a window fixing part which is screw-connected to the window barrel in order to fix the window part.

5. The apparatus for irradiating a laser of claim 1, wherein the anti-contamination cap includes:
an external insertion part to cover an outer periphery of the window barrel, when the anti-contamination cap is engaged with the window barrel;
an internal insertion part to be inserted into the window barrel, when the anti-contamination cap is engaged with the window barrel; and
a barrier film combined with an end of the internal insertion part, wherein a protrusion part to be engaged with a concave groove formed on an outer surface of the window barrel is formed on an inner surface of the external insertion part.

6. The apparatus for irradiating a laser of claim 4, further comprising:
a cover part connected to the front of the window barrel, wherein the cover part includes:
a cover fixing part formed on an inner periphery and engaged with a concave groove formed on an outer surface of the window barrel; and
a loss prevention wire of which one side is connected to the cover part and the other side is connected to the main body.

7. The apparatus for irradiating a laser of claim 1, further comprising:
a controller configured to control an operation of the apparatus for irradiating a laser,
wherein the controller includes:
a power switch configured to turn on and off a power supply;
an intensity selector configured to select an intensity of a laser beam output by the laser resonator; and
a display part configured to display the intensity selected by the intensity selector.

8. The apparatus for irradiating a laser of claim 7, wherein controller is located on a back surface of the main body facing a direction in which the laser beam is output.

9. The apparatus for irradiating a laser of claim 1, further comprising:
one or more of a grip sensor configured to detect a grip of an operator; and
a push sensor configured to detect a backward push of the beam barrel guiding unit.

* * * * *